United States Patent
Weitzman et al.

(10) Patent No.: US 12,188,886 B2
(45) Date of Patent: Jan. 7, 2025

(54) SYSTEM AND METHOD FOR DETECTING MICROBIAL AGENTS

(71) Applicant: DI HEALTH LTD., Tel Aviv-Jaffa (IL)

(72) Inventors: Samuel Weitzman, Tel Aviv-Jaffa (IL); Raphi Hess, Tel Aviv-Jaffa (IL); Charles A Krul, Tel Aviv-Jaffa (IL); Michael Sidrov, Tel Aviv-Jaffa (IL); Moti Gadian, Tel Aviv-Jaffa (IL)

(73) Assignee: Nanoscout Holdings Pty Ltd., Prahran (AU)

( * ) Notice: Subject to any disclaimer, the term of this patent is extended or adjusted under 35 U.S.C. 154(b) by 416 days.

(21) Appl. No.: 17/877,883

(22) Filed: Jul. 30, 2022

(65) Prior Publication Data
US 2023/0041482 A1 Feb. 9, 2023

Related U.S. Application Data

(60) Provisional application No. 63/227,463, filed on Jul. 30, 2021.

(51) Int. Cl.
*G01N 23/2251* (2018.01)
*G01N 33/487* (2006.01)
*G06V 10/26* (2022.01)
*G06V 20/69* (2022.01)

(52) U.S. Cl.
CPC ....... *G01N 23/2251* (2013.01); *G01N 33/487* (2013.01); *G06V 10/267* (2022.01); *G06V 20/695* (2022.01); *G06V 20/698* (2022.01); *G06V 2201/03* (2022.01)

(58) Field of Classification Search
CPC ............. G01N 23/2251; G01N 33/487; G06V 10/267; G06V 20/695; G06V 20/698; G06V 2201/03
USPC ....................................................... 250/311
See application file for complete search history.

(56) References Cited

U.S. PATENT DOCUMENTS

| | | | |
|---|---|---|---|
| 2010/0240050 A1* | 9/2010 | Bhatia | C12Q 1/37 977/773 |
| 2020/0087628 A1* | 3/2020 | Villenave | C12N 5/0697 |
| 2021/0301098 A1* | 9/2021 | Manesis | A61L 31/10 |

* cited by examiner

*Primary Examiner* — Kiet T Nguyen
(74) *Attorney, Agent, or Firm* — Karthik Murthy; Murthy Patent Law Inc.

(57) ABSTRACT

A system for identifying microbial agents such as virus particles in a sample. The system includes at least one processing unit for identifying in an electron micrograph obtained from the sample a darker region and identifying virus particles within the darker region. The system can optionally include an electron microscope, a sample collector and sample treatment chamber.

20 Claims, 8 Drawing Sheets

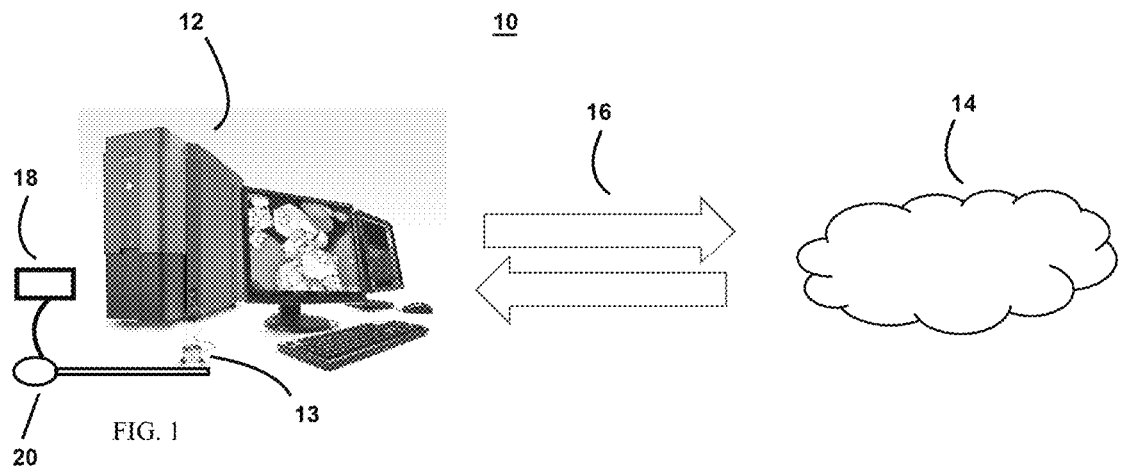
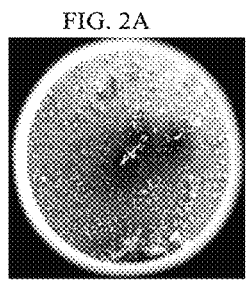 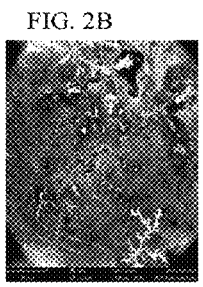 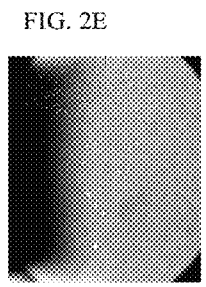
FIG. 2A  FIG. 2B  FIG. 2E
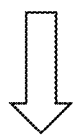 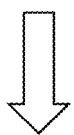
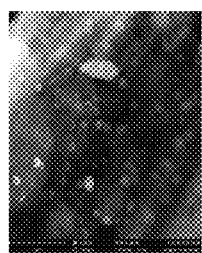 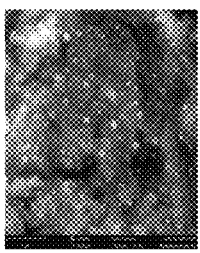 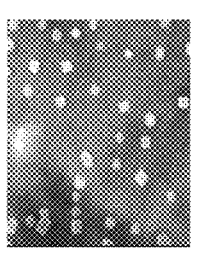 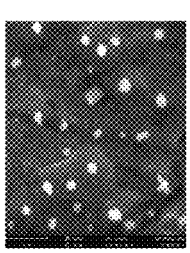
FIG. 2C  FIG. 2D  FIG. 2F  FIG. 2G FIG. 4A
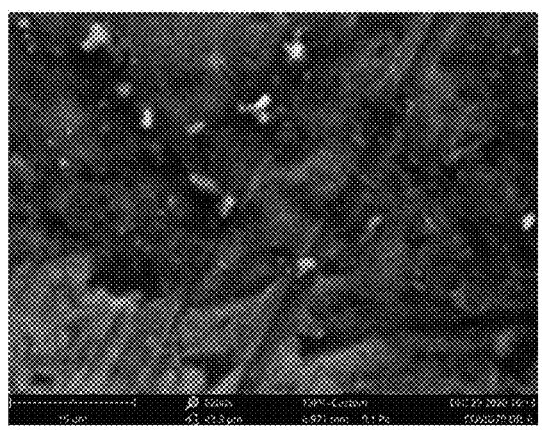
FIG. 4B
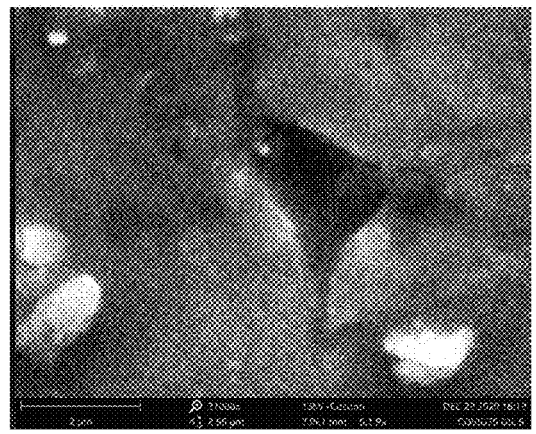
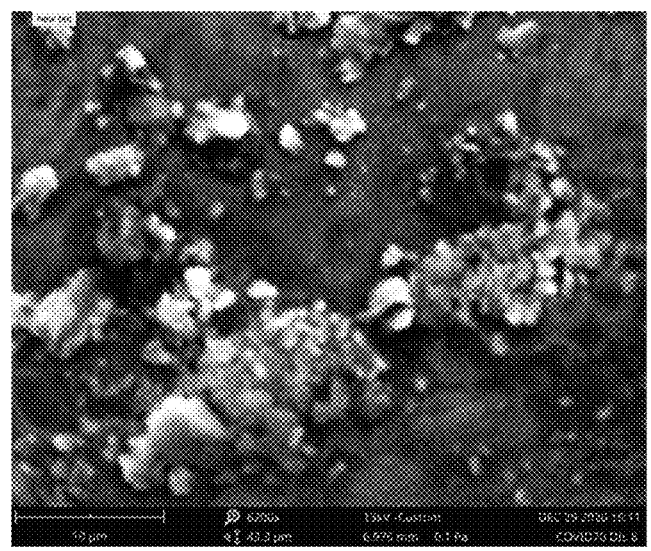
FIG. 4C FIG. 6A
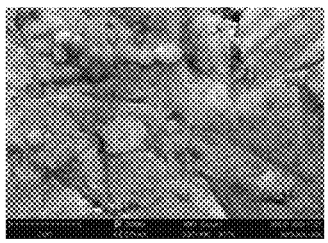
Pertussis
FIG. 6B
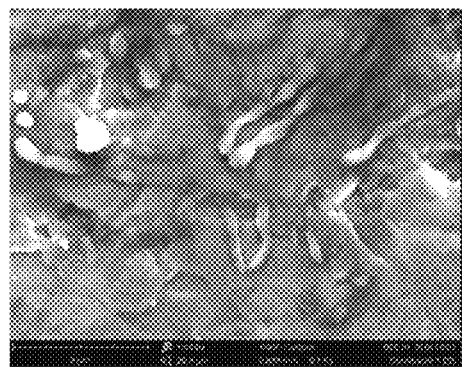
Haematobacter
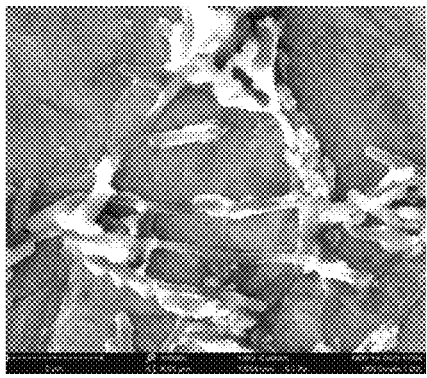
FIG. 6C
Cholera
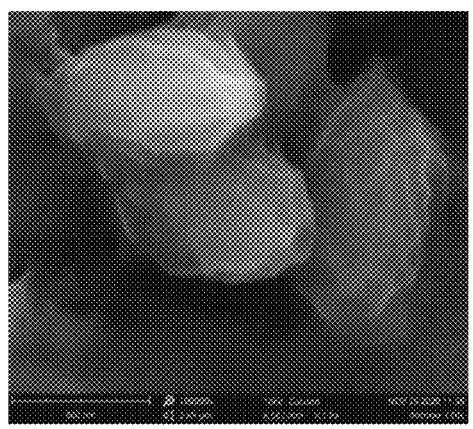
FIG. 6D
Anthrax
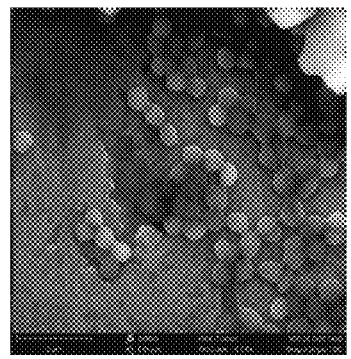
Legionella (legionnaires disease)
FIG. 6E
Streptococcus A
FIG. 6F

FIG. 6G FIG. 6H
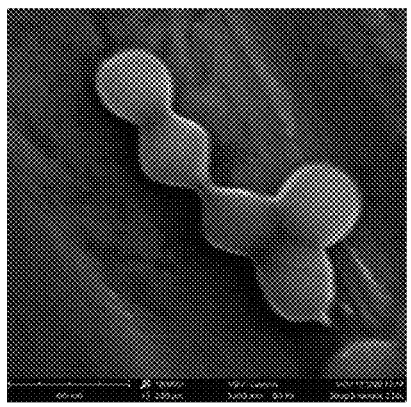 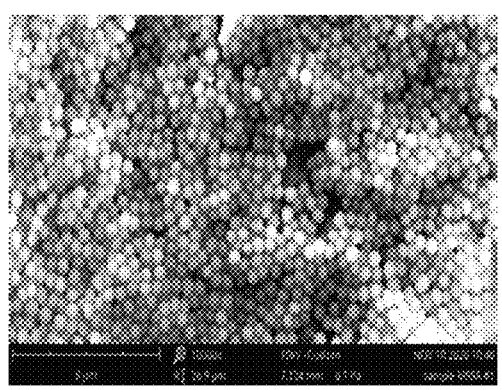
Streptococcus B     MSSA
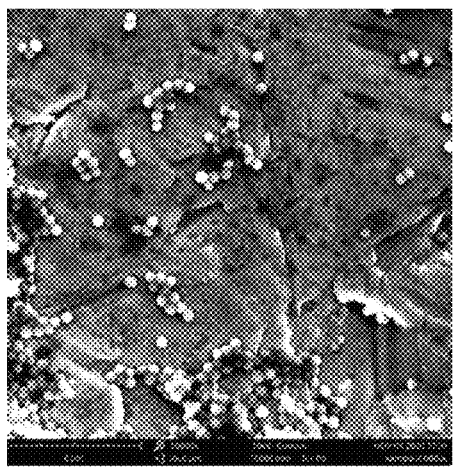 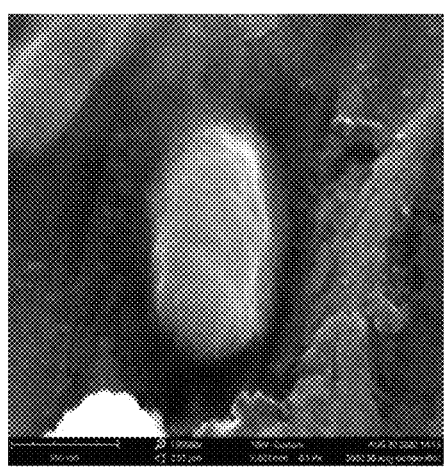
MRSA    FIG. 6I    E. Coli    FIG. 6J
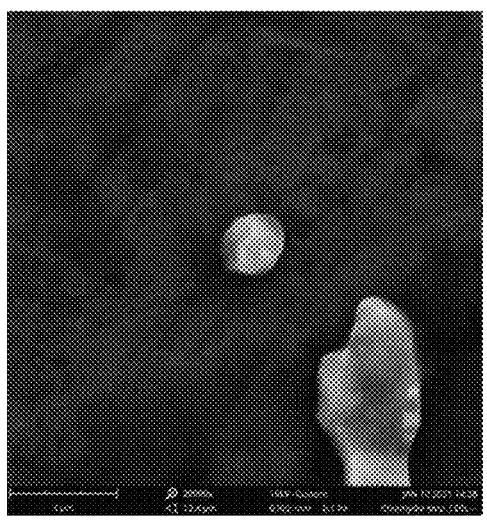 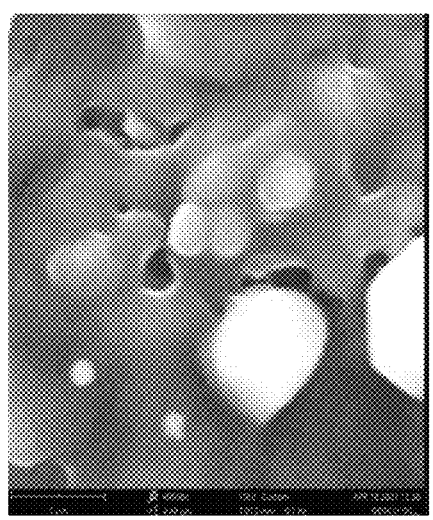
Chlamydia    FIG. 6K    Gonorrhea    FIG. 6L

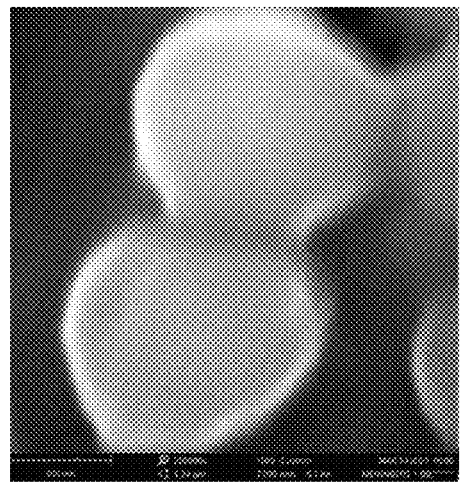
Meningitis     FIG. 6M

| Stub Quality | Original Stub Image | Stub Image with Edges Highlighted | Mean Row Intensity (MRI) Criterion |
|---|---|---|---|
| Good | 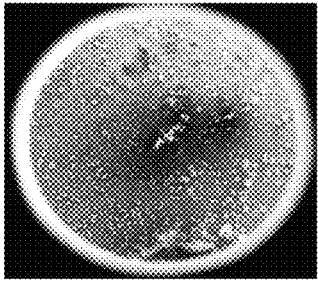 | 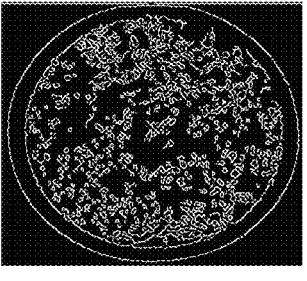 | 10343.38 |
| Bad | 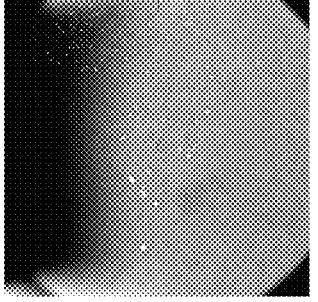 | 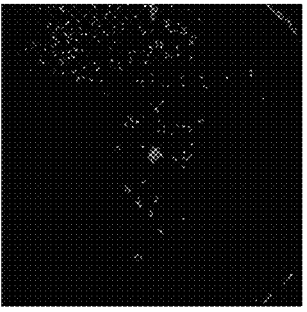 | 1600.18 |
FIG. 7

SYSTEM AND METHOD FOR DETECTING MICROBIAL AGENTS

BACKGROUND

The present invention relates to a system for detecting microbial agents such as viruses and bacteria in a sample. Embodiments of the present invention relates to the detection of Coronaviruses in a biological sample using electron microscopy. Throughout history, millions of people have perished from bacterial and viral infections. Viral infections have been responsible for several life-threatening human diseases including the 1918-1919 "Spanish flu", the HIV/AIDS epidemic, and the more recent Coronavirus outbreaks (SARS, MERS and SARS-CoV-2).

The SARS-CoV-2 pandemic has renewed interest in the need for approaches that can be used to identify viruses in biological samples rapidly. Since early 2020, the unprecedented response of the scientific and medical communities to the SARS-CoV-2 pandemic resulted in numerous publications that highlighted the urgent need to demonstrate and verify the presence of Coronavirus directly in biological samples.

One approach that can be effectively used to identify pathogens such as viruses in biological samples is electron microscopy (EM).

Unlike biochemical tests that require reagents, and may yield false positive or false negative results, EM is a powerful diagnostic tool that can be used to rapidly and accurately identify pathogens in-situ in biological samples. While EM can be used to visualize Coronavirus particles in samples due to their unique morphological features, investigators have inaccurately reported subcellular structures, including coated vesicles, multivesicular bodies, and vesiculating rough endoplasmic reticulum, as Coronavirus virions in electron micrographs.

Thus, there remains a need for an electron microscopy system that can be used to accurately and rapidly detect coronavirus particles without the aforementioned limitations of prior art systems, as well as differentiate the Coronavirus virions from other microbial agents and subcellular organelles.

SUMMARY

According to one aspect of the present invention there is provided a system for identifying a microbial agent in a sample comprising at least one processing unit for identifying in an electron micrograph obtained from the sample a darker region; and identifying microbial agent particles within the darker region.

According to embodiments of the present invention the system further comprises an electron microscope for providing the electron micrograph.

According to embodiments of the present invention the electron microscope is a scanning electron microscope.

According to embodiments of the present invention the at least one processing unit is configured for cropping the electron micrograph around the darker region prior to (b).

According to embodiments of the present invention the system comprises a first processing unit for identifying and cropping the darker region and a second processing unit for identifying virus particles within the darker region.

According to embodiments of the present invention the second processing unit is in communication with the first processing unit through a communication network.

According to embodiments of the present invention the at least one processing unit is further configured for cropping the darker region around individual virus particles.

According to embodiments of the present invention the processing unit is configured for identifying a coronavirus.

According to embodiments of the present invention the microbial agent is SARS-COV-2.

According to embodiments of the present invention the system further comprises a collection port for collecting the sample.

According to embodiments of the present invention the collection port is configured for collecting a liquid sample.

According to embodiments of the present invention the liquid sample is a biological sample.

According to embodiments of the present invention the biological sample is saliva or a mucous swab (e.g., nasopharyngeal swab).

According to embodiments of the present invention the system further comprises a chamber for fixing the sample.

According to embodiments of the present invention the chamber exposes the sample to 70-90% ethanol or methanol.

Unless otherwise defined, all technical and scientific terms used herein have the same meaning as commonly understood by one of ordinary skills in the art to which this invention belongs. Although methods and materials similar or equivalent to those described, herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 schematically illustrates an embodiment of the present system.

FIGS. 2A-D illustrate an electron micrograph showing a dark region (FIG. 2A) selected for cropping and magnification according to the teachings of the present invention (FIG. 2B) and a magnified image of the dark region showing presence of virus particles (FIGS. 2C-D).

FIGS. 2E-G illustrate an electron micrograph showing a dark region not selected by the present approach (FIG. 2E) and a magnified image of this dark region showing absence of virus particles (FIG. 2F-G).

FIGS. 4A-C illustrate 3 images of non-dark regions of an SEM image showing the absence of virus particles.

FIGS. 6A-M illustrate electron micrographs of bacteria identified in darker regions of SEM images using the present approach.

FIG. 7 illustrates SEM images of high quality (top left) and low quality (bottom left) and their highlighted edges (top right and bottom right respectively).

DETAILED DESCRIPTION

Figure 3A:
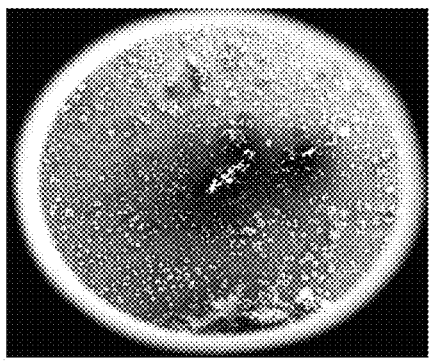
FIGS. 3A-D illustrates the process of dark region identification (FIG. 3B) from an SEM image (FIG. 3A), dark region magnification (FIG. 3C) and virus detection (FIG. 3D).

The present invention is of a system which can be used to detect microbial agents in a sample such as a biological sample. Embodiments of the present invention can be used to detect Coronaviruses in a scanning electron micrograph obtained from a biological sample such as a nasopharyngeal (NP) swab and saliva.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

One of the lessons from the SARS-CoV-2 outbreak of 2019 is that responding to a viral outbreak characterized by rapid transmission requires rapid identification of the infected individuals to enable isolation and contact tracing.

Different diagnostic tests that employ serological, molecular, and nanotechnology techniques have been developed for SARS-CoV-2. Tests that employ electron microscopy have also been suggested, but have not been employed commercially.

Scanning electron microscopy (SEM) is a powerful tool for microbiological research and diagnosis of infectious diseases. Electron microscopy can theoretically be used for ultra-rapid imaging of SARS-CoV-2 in biological samples, and thus has the potential to be a first line diagnosis approach for pandemic outbreaks. However, recent studies suggest that subcellular structures, including coated vesicles, multivesicular bodies, and vesiculating rough endoplasmic reticulum can be misidentified as coronavirus particles in electron micrographs.

In an effort to improve the reliability of EM diagnosis of coronaviruses, and while reducing the present invention to practice, the present inventors uncovered that crater-like-shaped dark regions found in scanning electron micrographs are more densely populated with microorganisms such as coronaviruses than relatively lighter regions. This discovery has led to the development of a novel approach for rapidly and accurately identifying microorganisms such as coronaviruses in a sample such as a biological sample.

Thus, according to one aspect of the present invention, there is a provided system for identifying microorganisms such as viruses, bacteria and fungi in a sample.

As used herein, the phrase "sample" can refer to a biological sample obtained from a body of an animal such as a human. A biological sample can be a surface swab, a tissue sample, a saliva sample, a mucous sample, a urine sample, a blood sample and the like.

The sample can also be obtained from the environment, e.g., from the surface of objects touched by humans (e.g., tables, door handles and the like).

As used herein the phrase "microbial agent" refers to any sub-multicellular biological entity with basic reproductive capabilities. Examples of microbial agents include, but are not limited to, bacteria, archaebacteria, microscopic fungi (such as yeasts), microscopic eukaryotes (e.g., "protozoa" and algae), and viruses.

Referring now to the drawings, FIG. 1 illustrates one embodiment of the present system which is referred to herein as system 10.

System 10 includes a processing unit 13 (e.g., desktop computer 13) configured for identifying, in an electron micrograph obtained from the sample, a darker region and identifying microorganisms such as virus particles within the darker region. An example of an algorithm developed by the present inventors specifically for identifying darker regions within an SEM is provided in Example 2 hereinbelow. The darker regions are typically 20-1000 times darker than surrounding regions, and are dependent on the threshold which we control (i.e., the lower the threshold required—the less area potentials for the search), and are amorphous in shape. The darker regions can be characterized by contrast from surrounding regions in which is seen and caused by the topology of the samples. One is able to see larger crystals, debris and brighter regions once the SEM has moved over to the Secondary Electron Detector (SED). In the field of view there may be numerous or minute amounts of these darker regions, however the search is still capable of finding virions in those locations. In most, if not all cases, the darker regions in the outset of testing will look like large or small craters.

To identify the darker regions, a standard image processing technique for edge detection can be utilized with a gradient-based algorithms (e.g., Canny Edge Detector).

The image itself is first processed to make sure the image quality is sufficient for further processing. An image of higher structural information ('high quality') is preferred.

A heuristic for gauging this property was developed and used to measure the mean intensity of the line sums of the image where only the edges of the objects contained in the image are highlighted. An image which contains more "black regions" will have more highlighted edges (i.e., higher mean intensity of the lines in the image).

An example is shown in FIG. 7. The top row illustrates a high quality image on the left, and its corresponding highlighted edges on the right. The bottom row illustrates a low quality image on the left and the corresponding edges on the right. The corresponding mean line intensity for the two images is presented at the last column.

The image quality validation steps can be carried out as follows:

(i) Convert the image to grayscale.

(ii) Apply a gaussian blur filter on the image (to eliminate the high frequency information which may interfere with the edge detection).

(iii) Run Canny Edge Detection on the blurred image.

(iv) Sum all the intensities of the pixels (line sums) in the edge-highlighted image and compute the mean of the 1D vector of those sums.

(v) Compare the value of 4 to a threshold representing a quality image.

(vi) Images matching or exceeding the threshold are further processed to identify the darker regions.

Stubs producing low quality images can be reimaged under different kV settings (intensity of the microscope electron beam), and the point-size parameters, which both control the image quality produced by the microscope.

Alternative approaches for identifying and optionally cropping-in darker regions of an electron micrograph include, for example, a grid search that scans the image with a window of a predefined size and searches each location covered by the window, or a variation of a random selection algorithm configured for identifying darker regions of an image System 10 can include an electron microscope 12 (OEM, SEM) for providing the electron micrograph of 10,000-270,000 magnification of samples. The electron microscope can be integrated with a desktop computer 13 configured for controlling microscopy functions and providing darker region identification and optionally cropping. An example of an SEM system (microscope and computer) suitable for use with the present system is a tabletop SEM system such as the Phenom Pharos Desktop™ SEM manufactured by ThermoFisher Scientific or the EM-30 Series made by Coxem.

Desktop computer 13 can also be configured for identifying microorganism particles within the darker region. Example 1 hereinbelow describes an algorithm developed by the present inventors for identifying and characterizing coronavirus and bacterial particles in an SEM.

Alternative approaches for identifying microorganisms in the darker region can employ algorithms for identifying particles of a specific shape, surface and internal features and diameter. For example, in the case of SARS-CoV-2, particles that are roughly spherical have Capsid and outer membrane, crown, and are about 150-250 nm in diameter can be classified as coronavirus particles using a simple template matching algorithm (comparing each crop of the original image to a predefined image of the searched item and measuring the degree with which it fits the template, based on some "goodness of fit" criterion e.g., Mean Squared Error of the intensity difference etc.).

Table 1 below provides shape and size parameters for bacteria that can be identified by the present system, FIGS. 6A-X are SEM images representing some of these bacteria.

TABLE 1

| | Bacteria | Shape | Size |
| --- | --- | --- | --- |
| 1 | TB | Rod Shaped | 2-4 micrometers in length and 0.2-0.5 um in width. |
| 2 | Chlamydia | Coccoid | 0.6 μm |
| 3 | Pertussis | Coccoid | 0.8 μm by 0.4 μm |
| 4 | Gonorrhea | Diplococci | 0.6 to 1.0 μm |
| 5 | Anthrax | Rod-shaped, Wrinkled like a date. | 2-4 micrometers in length and 0.2-0.5 um in width. |
| 6 | Cholera | Comma shaped | 1-3 μm in length by 0.5-0.8 μm |
| 7 | Legionnaires | Elongated irregular | 2 to 20 μm |

TABLE 1-continued

| | Bacteria | Shape | Size |
| --- | --- | --- | --- |
| 8 | Meningitis | shaped Bacilli Diplococci | 0.6 to 1.0 μm |
| 9 | MRSA | Cocci | 7-12 μm |
| 10 | E Coli | Bacilli | 1.0-2.0 micrometers × 0.5 micrometers. |
| 11 | MSSA | Diplococci | 7-12 μm |
| 12 | Haemophilus influenzae | Coccibacilli | 1 μm × 0.3 μm |
| 13 | Listeria | Chained bacilli | 0.5-4 μm in diameter and 0.5-2 μm in length |
| 14 | Strep A (GAS) | Cocci chains | 0.5-2.0 μm |
| 15 | Strep B (GBS) | Cocci chains | 0.5-2.0 μm |

According to one embodiment of the present invention, system 10 (on-site) provides complete diagnostic services from sample to detection and characterization of the microorganism.

According to another embodiment of the present invention, system 10 can be configured for remote identification of the microorganism in the sample.

In such a remote configuration, system 10 can include a cloud database server 14 which is in communication with desktop computer 13 through a communication network 16. Desktop computer 13 controls the microscopy functions (image acquisition) of microscope 12 and executes the algorithm for darker region identification and cropping. Once an EM image is cropped it is communicated from desktop computer 13 to database server 14 via a communication network for off-site identification and characterization of the microorganism(s) in the sample.

Darker region identification and cropping provides several advantages to both the local and remote configurations of system 10. Cropping the image down to 6.25-25% of its original size (in case of original image of 1024×1024 pixels, and crops of size ranging from 64×64 to 256×256 pixels) reduces file size and area and enables digital magnification to zoom in on individual vines particles. The smaller file size significantly decreases processing times as well as file transfer times from desktop computer 13 to database server 14.

Additional advantages of system 10 include:

(i) Protocol is quicker than current sample testing protocols;

(ii) Single protocol for all microbial agents;

(iii) Results within minutes;

(iv) Processing can be carried offsite;

(v) New pathogens can easily be detected without need for new reagents;

Database server 14 includes a processing unit for executing an algorithm for identifying a microorganism (e.g., coronavirus in the cropped image). Such identification can be preceded by further cropping of the image to isolate individual particles (see Example 3). One example of an algorithm suitable for identification of viruses and bacteria is provided in Example 1.

As is mentioned hereinabove, the present system can be used with any sample whether collected from a person or an object.

One sample that can be rapidly processed by the present system is a saliva sample. The present approach is highly sensitive and can be used to detect individual particles even when within host cells. As such, a saliva sample which is easy to obtain and process, can be used with the present system.

Thus, the present system can include a liquid collection port 18 for providing a liquid biological sample such as a saliva and NP swab sample to electron microscope 12.

While port 18 can provide the sample directly to electron microscope 12, the present inventors have discovered that prior fixation of the sample with 70% ethanol preserves the morphology for detection and the reaction of the sample and ethanol can enhance the appearance of the darker regions in the initial electron micrograph.

Thus, system 10 can further include a chamber 20 for fixing the sample collected by port 18. Once fixed the sample can then be manually/automatically transported to the microscope objective for micrograph capture (arrow).

Alternative approaches for fixing the sample include, for example, fixation with 70, 80, 90 or 95% ethanol, formaldehyde, formalin, glutaraldehyde, 2-propanol, 1-propanol or hydrogen peroxide.

Sample collection and processing can be carried out as described in Example 3 hereinbelow.

Table 2 below lists average times for each step from sample collection to cloud uploading of results.

System 10 was used for identifying coronavirus particles in biological samples obtained from infected and healthy individuals. As is described in Example 3 hereinbelow system 10 is a highly accurate diagnostic tool for coronavirus identification. Since electron microscopy of a sample can be carried out in <1 minutes from sample imaging to identification, the present system also provides a highly rapid diagnostic tool that can be used in settings that require rapid testing such as airports and the like.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non-limiting fashion.

Example 1

Virus Detection Algorithm

An algorithm for identifying microorganisms in a sample was developed. Scanning electron micrographs of samples of 24 positive samples containing SARS-COV-2 were obtained, as well as samples containing 18 pathogenic bacteria.

In addition to the samples in the original test set, cocci, bacilli, background, and unknown bacteria were used to test the accuracy of the model. The model was built by taking images of virus or bacteria that have been cropped to fit the virion or bacteria in the image, through a blob. The blobs are circular boundaries that will fit to the radius or area of the virus or bacteria in question. The cropped images were sorted into annotated files that were used for classification. The algorithm was trained using these annotated files to distinguish between SARS-CoV-2 and other microbial agents. Approximately 2681 images including SARS CoV-2 (1870), Cocci Bacteria (221), Bacilli Bacteria (105), Unknown Bacteria (248) and negative Samples (237) were processed and used to train the algorithm.

The initial version of the algorithm was then given a test set and the results were as follows:

SARS-CoV-2 Virions Recall: 93%, Precision: 91%
Bacteria Recall: 91%, Precision: 95%
Negative Recall: 99%, Precision: 97%
  Overall Accuracy of Model 94%

Figure 5:
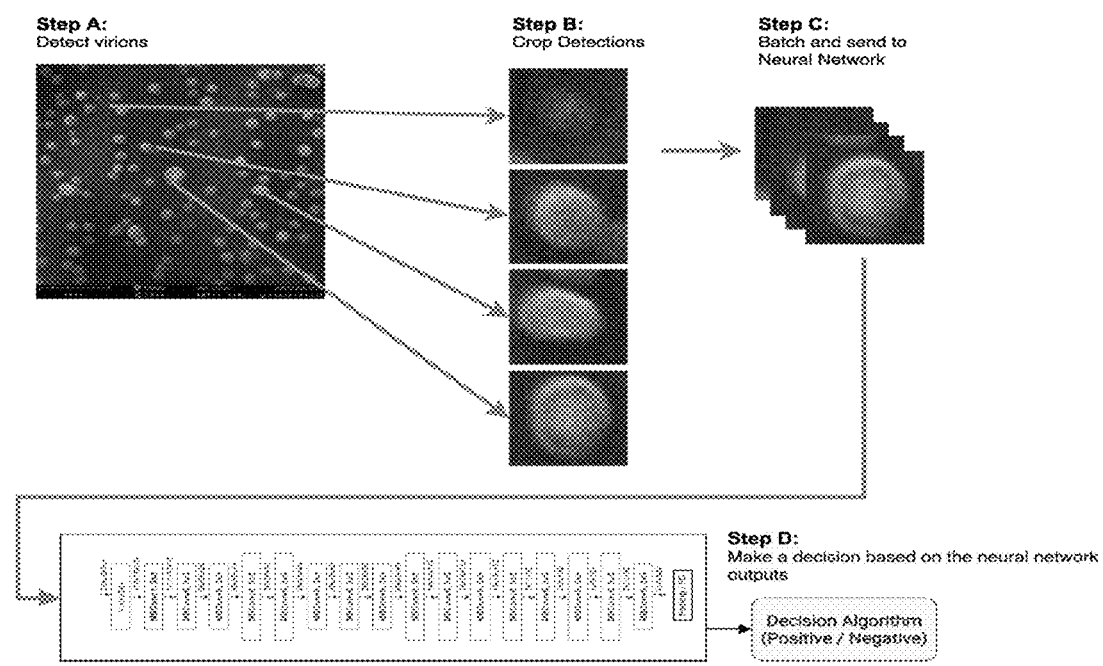
FIG. 5 illustrates the present approach for detecting viruses in an electron micrograph obtained from a biological sample.

FIG. 5 summarizes the present approach for identifying Coronavirus virions in an SEM image. To detect the virions, we will use a Convolutional Neural Network (CNN), which is a special type of Neural Network for problems which involve visual data.

CNN, as most of the neural networks, is a feed-forward network, which is built in a layered manner (i.e., each layer has input and output, which is then fed into the next layer). CNN basically "summarizes" structural features of the image into a compact representation, whereas the data flows deeper—the network recognizes more general features, as its' resolution increases (i.e., in the earlier layers the network may recognize lines and curves, while in the deeper layers it summarizes those to shape more sophisticated objects, which then may be used for indication if it is a pathogen or not).

Prior to use in detection the CNN is trained on data to adjust the weights of the network. The process for identifying the coronavirus virions may be summarized as follows:

(i) Split the dataset into train and test sets, where the former is used for models' weights fixing, and the latter for performance assessment;
(ii) Augment the training dataset, i.e., make the data more versatile by applying different transformations of the images (e.g., rotation, random crop etc.). This is done in order to make the model more robust to noise (e.g., different image settings which may appear in real life data);
(iii) Teach the model by adjusting the weights; and
(iv) Assess the accuracy of the model on the test data (i.e., data which was set aside, and which the network has never seen before). This step is basically a simulation of a real-time setting, and may present the accuracy which may be expected when the network is integrated into production.

The Detection Pipeline phase includes 4 steps, Blob detection, Cropping, Classification and Decision algorithm.

Blob Detection

The input for this step is the .tiff image that acquired from the SEM, from this image the virion locations are detected in the image using a naive blob detection algorithm.

Cropping

The objects located by the detector will be cropped, and preprocessed for the neural network (for example, resized to a fixed shape).

The crops will be batched in order to be sent to the trained neural network for classification Classification The batched crops send to the trained neural network and get label (i.e. classification) and score (i.e. classification probability) for each.

Decision Algorithm

Once all crops taken from the image are classified, a decision algorithm (basically a simple logic of rules) decides how to classify the whole image based on the outputs from the neural network.

A rapid inactivation/fixation protocol that includes exposing the sample to 70% ethanol was tested on 18 pathogenic bacteria. The fixed samples were imaged under an SEM and distinguishing factors were identified in all of the samples in a reliable and reproducible manner using the present algorithm. Table 2 below lists the bacteria imaged and the number of times each bacteria was sampled.

TABLE 2

| | Bacterial Sample | Sample number (Stubs) |
|---|---|---|
| 1 | TB | 2 |
| 2 | Chlamydia | 2 |
| 3 | Pertussis | 2 |
| 4 | Gonorrhea | 2 |
| 5 | Anthrax | 2 |
| 6 | Cholera | 2 |
| 7 | Legionnaires | 4 |
| 8 | Meningitis | 2 |
| 9 | MRSA | 4 |
| 10 | MSSA | 4 |
| 11 | Strep A | 2 |
| 12 | Strep B | 2 |
| 13 | Haematobacter | 4 |
| 14 | Bacilli (E. Coli)* | 6 |
| 15 | Bacteria - Unknown | 6 |
| 16 | Background/Negative | 2 |
| 17 | Haemophilus influenzae | 2 |
| 18 | Listeria | 2 |

Example 2

Darker Region Algorithm

In an effort to minimize processing time and maximize accuracy of results, the present inventors scanned thousands of SEM images in order to identify image characteristics that would enhance detection of microbial agents.

Figure 3B:
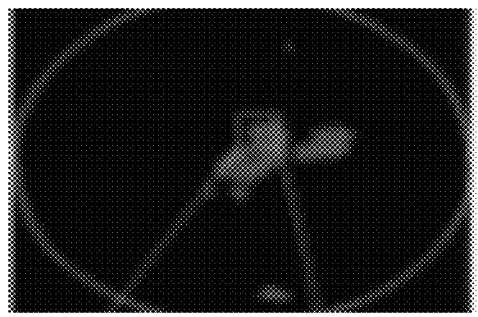
Figure 3D:
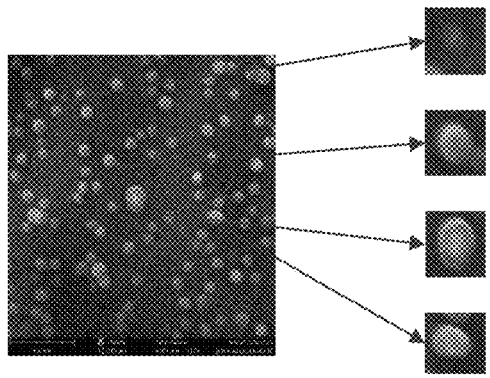
Figure 3C:
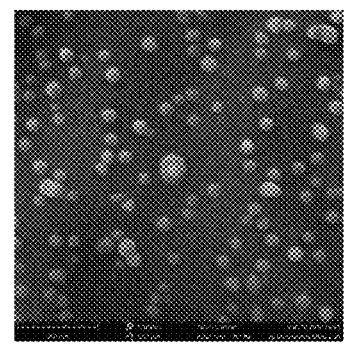

When looking at live microscope images, the present inventors noticed the appearance of darker regions (FIGS. 2A-B) interspersed between lighter regions (FIGS. 2E-G). Further microscopic analysis of these darker regions (FIGS. 3A-B) (as well as the lighter regions) under higher magnification (FIG. 3C) showed that these darker regions are highly populated with what appears to be virus particles. In fact, the darker regions were 15 times more populated with virus particles that similarly sized lighter regions (FIGS. 4A-C).

The magnified image was cropped around single particles (FIG. 3D) and analyzed using the present algorithm. All of the cropped particles turned out to be SARS-CoV-2 particles.

Analysis of bacterial samples provided similar results. FIGS. 6A-M illustrate bacterial particles found in darker regions of an SEM image.

This discovery led to the development of a darker region finding algorithm that can be used with the present algorithm (Example 1) to efficiently and rapidly detect and identify SARS-CoV-2 as well as other viruses and bacteria.

The darker region algorithm converts the SEM image from RGB to greyscale and then highlights edges of darker regions. The darker regions are then isolated and cropped and the cropped regions are magnified at 20,000-200,000 times to identify particles using shape and size criteria. Images with no particles matching the criteria are discarded. Images with particles can be further analyzed by a microbe-specific algorithm such as that described in Example 1 to identify the particles.

Example 3

Identification of Viruses in Biological Samples

The algorithms of Examples 1 and 2 can be used to analyze patient samples for the presence of virus and bacteria.

A tube that includes 0.70 ml of Ethanol is used to collect patient saliva samples to a predetermined final volume of 1 ml. The patient then flips the closed tube vertically 3 times to make sure the saliva and ethanol are properly mixed. Approximately >200 microliters of the sample are pipetted onto an aluminum stub and the sample is then dried in a desiccator for 12-15 minutes to make sure that it contains no liquid at all and the sample is completely dry.

The stub is then placed on the sample holder of the microscope and imaged and processed using the darker image algorithm of Example 2.

Once an initial image is captured, the system is switched over to electron microscopy (EM) at a setting of 10 kV and a spot size of 1.

The darker regions are then identified using the algorithm of Example 2 and the system is switched to 80,000-100,000 magnification to determine presence or absence and possibly count of particles. Images with particles are then further processed (locally or by a cloud server) to identify the particles.

The above procedure was tested on 28 samples resulted in 94% accuracy in identifying Coronavirus particles (Table 3).

TABLE 3

| Pathogen | Sample Size | Number of images |
|---|---|---|
| SARS-CoV-2 | 12 | 1870 |
| Negative SARS-CoV-2 | 2 | 237 |
| E. Coli (Bacilli) | 6 | 105 |
| MRSA (Cocci) | 6 | 221 |
| Unknown Bacteria | 6 | 248 |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for identifying a microbial agent in a sample comprising at least one processing unit for:
    (a) identifying in an electron micrograph obtained from the sample a darker region; and
    (b) identifying microbial agent particles within said darker region.

2. The system of claim 1, further comprising an electron microscope for providing said electron micrograph.

3. The system of claim 2, wherein said electron microscope is a scanning electron microscope.

4. The system of claim 2, wherein said at least one processing unit is configured for cropping said electron micrograph around said darker region prior to (b).

5. The system of claim 4, comprising a first processing unit for identifying and cropping said darker region and a second processing unit for identifying virus particles within said darker region.

6. The system of claim 5, wherein said second processing unit is in communication with said first processing unit through a communication network.

7. The system of claim 4, wherein said at least one processing unit is further configured for cropping said darker region around individual virus particles.

8. The system of claim 1, wherein said processing unit is configured for identifying a coronavirus.

9. The system of claim 8, wherein said microbial agent is SARS-COV-2.

10. The system of claim 1, further comprising a collection port for collecting the sample.

11. The system of claim 10, wherein said collection port is configured for collecting a liquid sample.

12. The system of claim 11, wherein said liquid sample is a biological sample.

13. The system of claim 12, wherein said biological sample is saliva or mucous.

14. The system of claim 10, further comprising a chamber for fixing the sample prior to (a).

15. The system of claim 14, wherein said chamber exposes the sample to 70% ethanol.

16. The system of claim 1, further comprising a collection port for collecting the sample;
further comprising a chamber for fixing the sample prior to (a);
wherein said chamber exposes the sample to 70% ethanol.

17. The system of claim 1, further comprising a collection port for collecting the sample;
wherein said collection port is configured for collecting a liquid sample;
wherein said liquid sample is a biological sample;
wherein said biological sample is saliva or mucous.

18. The system of claim 1, further comprising an electron microscope for providing said electron micrograph;
wherein said at least one processing unit is configured for cropping said electron micrograph around said darker region prior to (b);
comprising a first processing unit for identifying and cropping said darker region and a second processing unit for identifying virus particles within said darker region;
wherein said second processing unit is in communication with said first processing unit through a communication network.

19. A method for identifying a microbial agent in a sample comprising at least one processing unit for:
(a) identifying in an electron micrograph obtained from the sample a darker region; and
(b) identifying microbial agent particles within said darker region;
further comprising an electron microscope for providing said electron micrograph;
wherein said electron microscope is a scanning electron microscope.

20. A method for identifying a microbial agent in a sample comprising at least one processing unit for:
(a) identifying in an electron micrograph obtained from the sample a darker region; and
(b) identifying microbial agent particles within said darker region;
further comprising an electron microscope for providing said electron micrograph;
wherein said at least one processing unit is configured for cropping said electron micrograph around said darker region prior to (b);
comprising a first processing unit for identifying and cropping said darker region and a second processing unit for identifying virus particles within said darker region;
wherein said second processing unit is in communication with said first processing unit through a communication network.

* * * * *